United States Patent [19]

Frost et al.

[11] 4,380,931
[45] Apr. 26, 1983

[54] APPARATUS AND METHOD FOR QUANTITATIVE NONDESTRUCTIVE WIRE TESTING

[75] Inventors: Harold M. Frost; James H. Prout; Robert W. Reed, all of State College, Pa.

[73] Assignee: The United States of America as represented by the Secretary of the Navy, Washington, D.C.

[21] Appl. No.: 256,750

[22] Filed: Apr. 23, 1981

[51] Int. Cl.³ ............................................. G01N 29/04
[52] U.S. Cl. ........................................ 73/643; 73/598; 73/599
[58] Field of Search ........... 73/643, 644, 600, 597–599

[56] References Cited

U.S. PATENT DOCUMENTS

| | | | |
|---|---|---|---|
| 3,850,028 | 11/1974 | Thompson et al. | 73/643 |
| 4,092,868 | 6/1978 | Thompson et al. | 73/643 |
| 4,164,873 | 8/1979 | Bottcher et al. | 73/643 |
| 4,307,616 | 12/1981 | Vasile | 73/643 |
| 4,312,231 | 1/1982 | Kawashima et al. | 73/643 |

OTHER PUBLICATIONS

Frost et al., "Velocity and Attenuation in Metal Waveguides," paper given in session Physical Acoustics IV; Ultrasonics and Materials, Acoustical Society of America Spring Meeting, Apr. 24, 1980.

*Primary Examiner*—Howard A. Birmiel
*Attorney, Agent, or Firm*—Robert F. Beers; Arthur A. McGill; Prithvi C. Lall

[57] ABSTRACT

An apparatus and method for quantitative nondestructive testing (NDT) of a wire wherein noncontacting ultrasonics is used. A transmitter-transducer coil is held in close proximity of a test wire or tube and high amplitude electrical current pulses are passed in the coil. A magnetic field perpendicular to the longitudinal axis of the wire is applied in the region. As a result of the electrical current pulses in the transducer coil, eddy currents are produced on the surface of the test wire. As a result of the magnetic field applied in the region, these eddy currents lead to Lorentz forces in the wire, which in turn generate corresponding torsional waves in the test wire. These waves speed down the wire and are received by a reciprocal transduction process, by means of a receiver-transducer. The velocity and attenuation measurements of the torsional waves along the axis of the test wire are made precisely and accurately via multiple-transducer setups. The data are interpreted in terms of the material conditions including mechanical defects or flaws in the test wire.

12 Claims, 13 Drawing Figures

APPARATUS AND METHOD FOR QUANTITATIVE NONDESTRUCTIVE WIRE TESTING

BACKGROUND OF THE INVENTION

This invention relates to systems for testing wires and, more particularly, for studying the characteristics of a stationary and/or moving wire using noncontacting ultrasonics.

Sensitive, selective and otherwise useable NDT methods for testing wires are scarce in comparison to such methods for metals in other geometries such as circular rods, tubes of relatively large diameter, plates, billets, forgings and weldments. Inspection of a wire rope by acoustic emission techniques has also been described in the prior art but not the inspection of a single wire. Some ultrasonic methods have also been used for testing wires. As an example, two piezoelectric transducers were coupled with oil between the working surface and the surface of a composite wire with a metal matrix. In such a method, a transmitter-transducer launches an ultrasonic pulse of frequency of a few megahertz (MHz) onto a test wire and the pulse is then picked up at some distance away by a receiver-transducer. However, velocity and attenuation measurements using such a method are not feasible, as the ultrasonic signals involved are not well defined. This is even more so in the case of a moving test wire, as in a production environment. Other contacting ultrasonic methods have been reviewed by Krautkrämer and Krautkrämer in Chapter 23 of the Handbook: Ultrasonic Testing of Materials, Second Edition (Springer-Verlag, N.Y., 1977) which is incorporated herein by reference. Such methods use continuous waves rather than pulses which lead to simultaneous generation of various acoustic modes which are not easily separable. Eddy current methods have also been used in an attempt to inspect for the condition of wire. Here, a small coil of fine gauge wire typically encircles the test wire. A small dynamic current in the coil generates eddy currents in the test wire. The coil has a measurable electrical impedance which is affected by the presence of the nearby metal surface of the test wire. The electro-magnetic wavelengths involved in such methods are several orders of magnitude larger than the acoustic wavelengths for these methods. Consequently, such methods are basically static in which the object to be tested is small in comparison with the wavelength involved. Furthermore, the eddy current methods also tend to have the drawback of the results being dependent upon the gap between the test wire and the transducer coil. In other words, as the conditions of clearance between the test wire and the coil change, the eddy current parameters change likewise. Furthermore, eddy current methods tend to inspect surface defects instead of volume defects and thus tend to be less suitable for detecting internal defects or flaws. Some of the eddy current test methods have been discussed in Chapters 40 and 42 of Volume 2 of "Nondestructive Testing Handbook," edited by R. C. McMaster (The American Society for Nondestructive Testing, Inc., Columbus, Ohio 1959) which is also incorporated herein by reference.

It appears that little prior work has been done for testing wires using noncontacting ultrasonic transducers. The transducers used for nondesctructive methods using noncontacting ultrasonics involve electromagnetic ultrasound transduction and are usually referred as EMT's in the literature. In a nondestructive test method of this type, EMT's are combined with an eddy current-type coil with a nearby permanent magnet. However, as pointed out in Krautkrämer et al, such a method involves the threading of the test rod through bore holes in the NDT system. For stock with rough surfaces and thus with rod diameters intermittently greater than the internal diameter of bore holes of the testing system, the feed-through motion of the stock has to be stopped to avoid damage to the system. Furthermore, some EMT methods for nondestructive testing send waves partly or completely in a direction transverse to the longitudinal axis of rods, tubes and other geometries. Other EMT methods require access to the ends of the test rod or tube. It is thus highly desirable to have an NDT method of testing stationary or moving test wires in a production environment which uses noncontacting ultrasonic transducers requiring access only to the sides of the test material and suitable for ultrasonic waves propagating along the longitudinal axis.

SUMMARY OF THE INVENTION

The objectives and advantages of the present invention are accomplished by utilizing a plurality of noncontacting ultrasonic transducers in cooperation with a magnetic field having a direction perpendicular to the longitudinal axis of the test wire. According to the teachings of the subject invention, a moving test wire extends through a gap provided by the pole pieces of a magnet and the coil, usually non-encircling, of a transducer. The testing system includes at least a transmitter-transducer and a receiver-transducer which are used to study the velocity and attenuation of torsional waves which are generated in the test wire when electrical pulses of high magnitude are passed through the coil of the transmitter-transducer. From the data of velocity and attenuation measurements of the torsional waves in the test wire, various characteristics of the test wire are obtained.

An object of the subject invention is to provide a unique means for nondestructive testing (NDT) of electrically conducting materials even if they are moving relative to the detecting system.

Another object of the subject invention is to use a noncontacting method of testing wires wherein the characteristic dimensions of the active areas of the noncontacting electromagnetic-ultrasound transducers (EMTs) are much smaller than the characteristic dimensions of the test wire.

Another object of the subject invention is to have an NDT system compatible with the wire production requirement and wherein the transducers can be brought into or removed from the proximity of the test material, during an ongoing inspection process.

Still another object of the subject invention is to have a NDT system which is capable of high spatial resolution (i.e., selectivity) in waveguide structures.

Another object of the subject invention is to have a NDT method wherein the data are independent of the gap between each transducer coil and the test material.

Still another object of the subject invention is to have a NDT method where the data is independent of the gap between each pole face of the magnet and the test material.

Still another object of the subject invention is to have a NDT method which has potentially high sensitivity for specific types of material conditions which need to be monitored.

Other objects, advantages and novel features of the invention will become apparent from the following detailed description of the invention when considered in conjunction with the accompanying drawings wherein:

DESCRIPTION OF A PREFERRED EMBODIMENT

Figure 1:
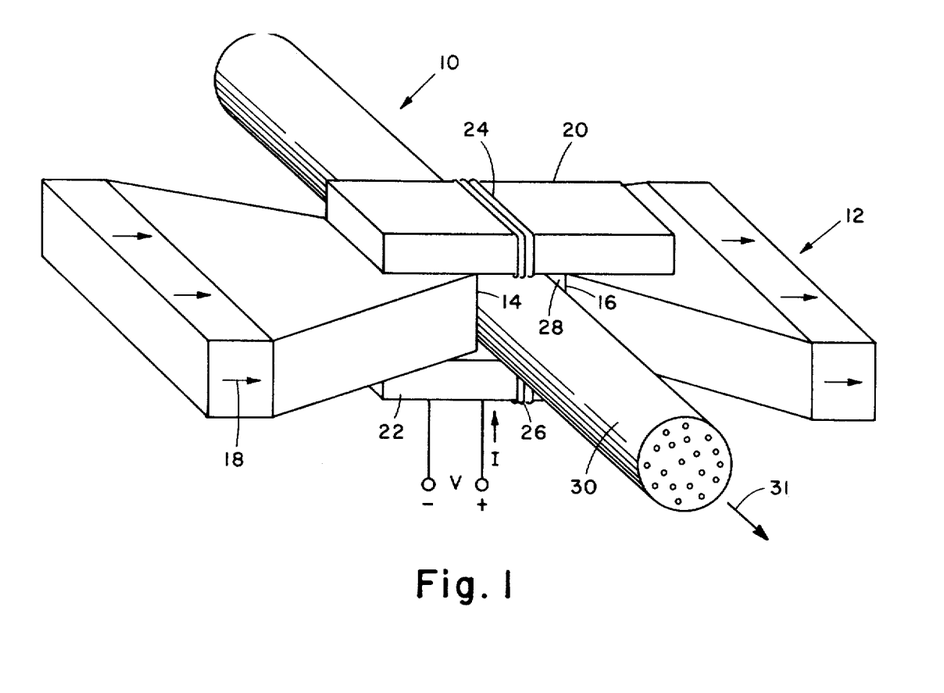
FIG. 1 is a perspective view of the apparatus used according to the teachings of the subject invention.
Figure 2:
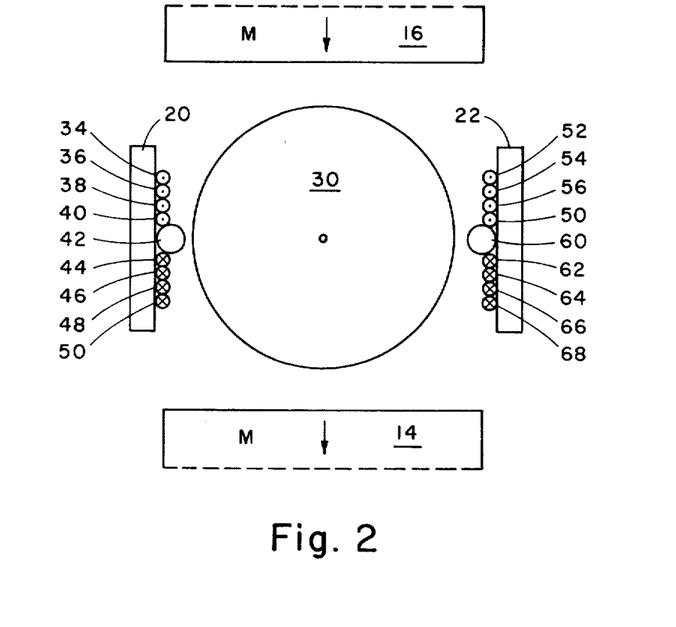
FIG. 2 is a schematic representation of a noncontacting electromagnetic torsional wave ultrasound transducer (EMT) for a test wire.
Figure 3:
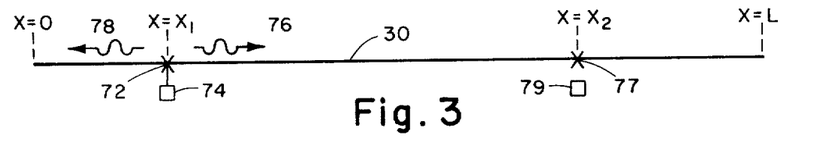
FIG. 3 is a diagrammatic representation of a system using one transmitter-transducer and one receiver transducer.

Referring to the drawings wherein like reference characters designate identical or corresponding parts throughout the several figures, and more particularly, to FIG. 1 thereof, a perspective view of the NDT system 10 according to the teachings of the subject invention is shown. The system 10 includes a magnet 12 with pole pieces 14 and 16 and having a magnetization axis shown by arrow 18. It further includes coil forms 20 and 22 for a transmitter-transducer having coils 24 and 26 respectively wound thereon. Coils 24 and 26 and pole pieces 14 and 16 form a gap 28 which is the gap through which test wire 30 is pulled as shown by arrow 31. FIG. 2 indicates an end view of test wire 30 placed in the gap provided by the transducer. The transducer as shown in FIG. 2 includes a magnet with pole pieces 14 and 16. FIG. 2 shows coil forms 20 and 22 and four transducer coil legs 34, 36, 38 and 40 which are wound by a nylon spacer 42. Coil legs 44, 46, 48 and 50 are likewise wound on coil form 20 on the opposite side of nylon spacer 42. In a similar fashion coil legs 52, 54, 56 and 58 are wound on coil form 22 on one side of nylon spacer 60 and coil legs 62, 64, 66 and 68 are wound on coil form 22 on the opposite side of nylon spacer 60. As can be seen from FIG. 2, the test wire 30 is placed in gap 65 of the transducer. When electrical pulses of high current amplitude (500 A) and short duration (i.e., a few μsec where 1 μsec=10$^{-6}$ sec) are passed through coil legs 34–40; 44–50; 52–58 and 62–68, eddy currents are generated on the surface of test wire 30 which, via the magnetic induction between pole pieces 14 and 16, apply torque on the test wire 30 and thus create torsional waves on the test wire 30 which propagate in the test wire along is longitudinal axis. (It should be noted that a different geometrical orientation for the transducer can also be used.) As shown in FIG. 3, a torsional wave starts in test wire 30 at point 72 which is close to the position of the transmitter-transducer coil 74. The torsional waves generated at point 72 in test wire 30 propagate in both directions as shown by arrows 76 and 78. Torsional wave represented by arrow 76 propagates in the direction of receiver-transducer coil 79 located at position 77 of the test wire 30.

Figure 4:
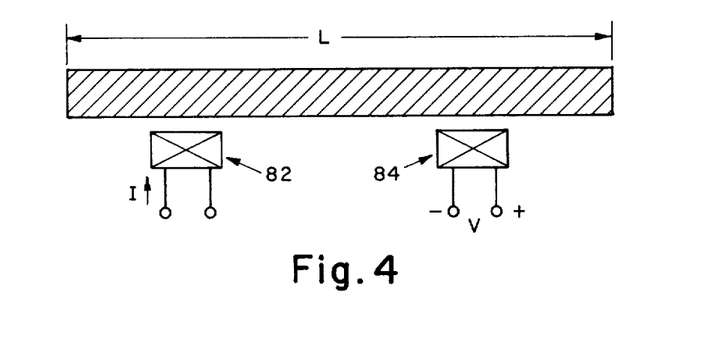
FIG. 4 shows a schematic version of a 2-transducer method.
Figure 5:
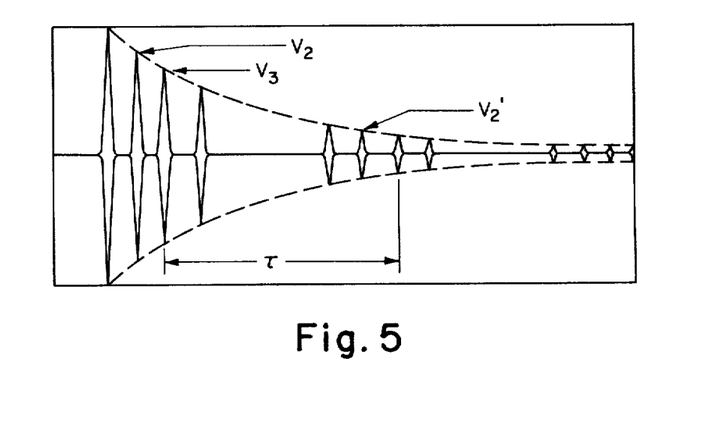
FIG. 5 is a graphical representation of the pulses in the NDT systems as shown in FIGS. 3–4.
Figure 7:
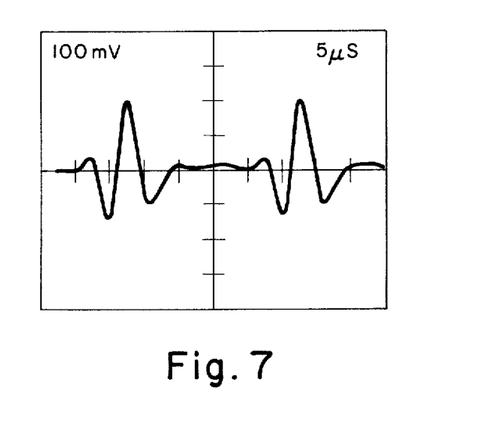
FIG. 7 is the graphical representation of electrical pulses for a test material of a short acoustic path length.
Figure 8:
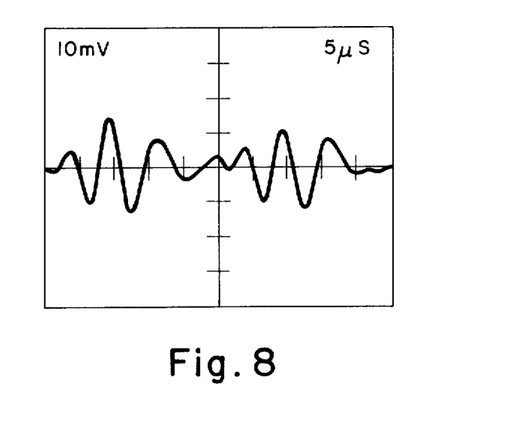
FIG. 8 is a graphical representation of electrical pulses generated by the receiver for a relatively much longer path length.

FIG. 4 schematically shows test wire 30 as acoustic medium of length L and transmitter-tranducer 82 and receiver-transducer 84 placed along the axis of test wire 30. FIG. 5 shows a corresponding train of pulses displayed on an oscilloscope. As shown in FIGS. 3 and 5, electrical pulses are generated in groups of 4 when end reflections are included and the velocity $\bar{c}'$ of the torsional wave can be obtained by dividing twice the length, L, of the test wire by the time period between the two positions of the same wave. This gives $2L/\tau$ where L and $\tau$ are shown in FIGS. 4 and 5. The system attenuation $\bar{a}'$ is depicted in FIG. 5. FIG. 7 shows the pulse amplitude as a function of time for a test wire of, in effect, short length (L) whereas FIG. 8 shows the amplitude variation of a torsional wave with time for a relatively long test wire of length L' (L'>>L). It is to be noted that the vertical scale used in FIG. 7 is 10 times larger than the corresponding scale in FIG. 8, yet the pulses are still resolved in time and have about the same shape. This is an example of evidence we have developed that the only acoustic wave mode involved is the lowest-order torsional wave mode, whose velocity of propagation is free of dispersion.

In Table 1 are shown velocity and attenuation data ($\bar{c}'$ and $\bar{a}'$) measured on short lengths of various wire materials by means of a 2-transducer setup, in comparison with plate and bulk values.

TABLE 1

| | PULSED ULTRASOUND DATA | | |
|---|---|---|---|
| MATERIAL | WIRE DIAMETER (mm) | VELO- CITY[a] (10$^3$ m/s) | ATTENUA- TION[a] (Nepers/m) |
| AL ALLOY WIRE | 1.1 | 3.0 | 0.034 |
| "GOOD" MMC[b] WIRE | 1.2 | 2.6 | 0.76 |
| "BAD" MMC[c] WIRE | 1.4 | 2.1 | 2.6 |
| MMC[b] PLATE | N/A | 2.8[c] | — |
| AL ALLOY (BULK) | N/A | 3.0[d] | 0.55[d] |

NOTES:
[a]1st order, 140 kHz torsional wave except as noted.
[b]Graphite/Al Metal Matrix Composite.
[c]Datum of Blessing, Elban, & Foltz (1978); at 10 MHz.
[d]From Viktorov (1978); at 1 MHz.

Figure 6:
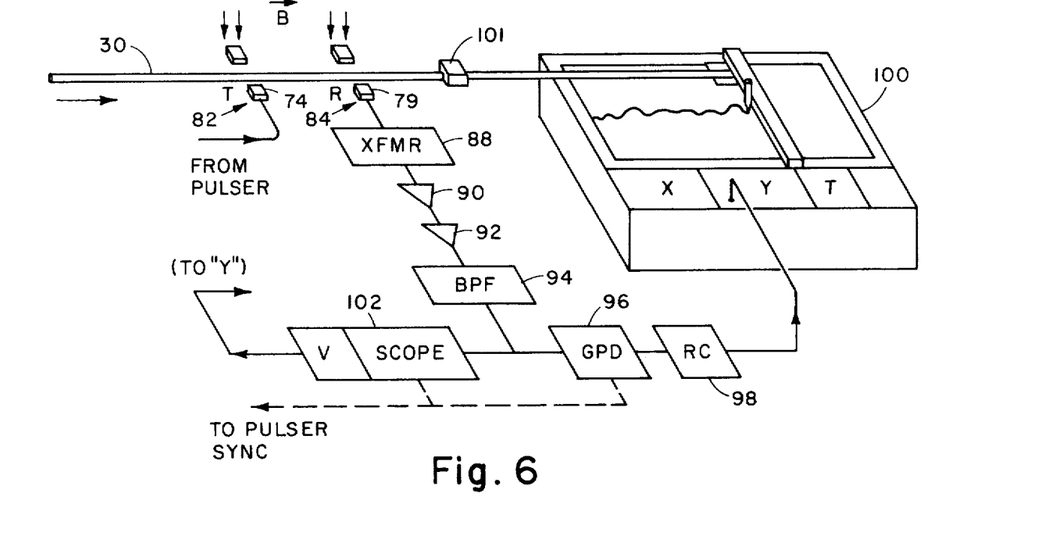
FIG. 6 is a block diagram for a simplified NDT system using a transmitter and a receiver.
Figure 9:
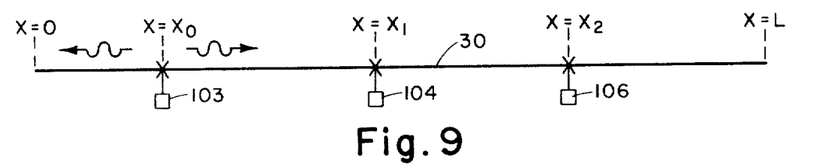
FIG. 9 is a schematic representation of a system using a 3-transducer method.
Figure 10:
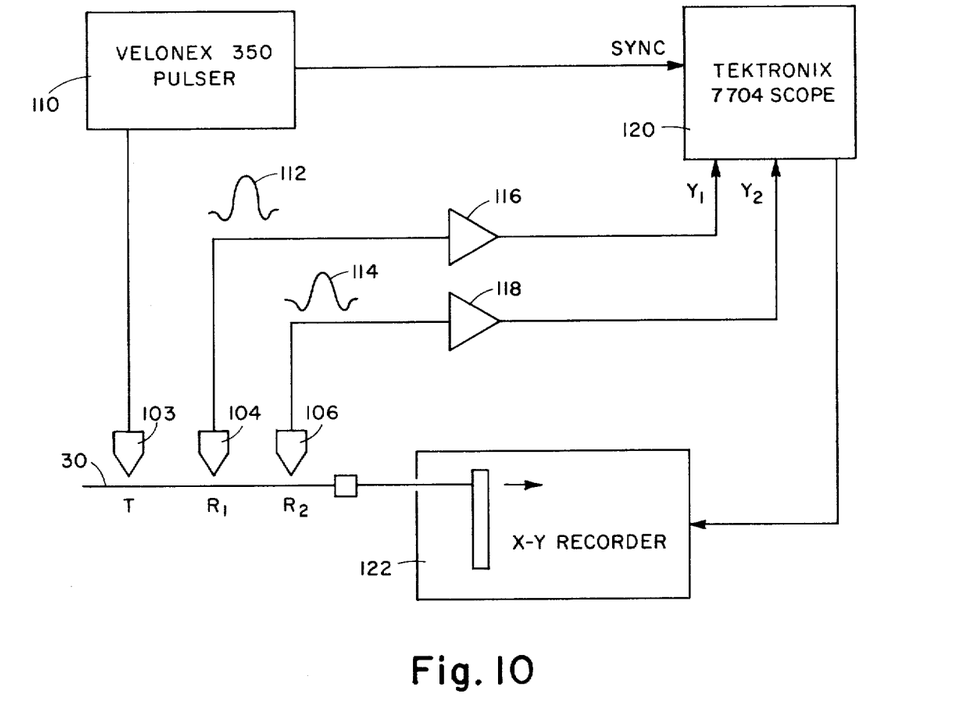
FIG. 10 is a simplified schematic representation of a velocity scan system using 3-transducers.

FIG. 6 depicts a setup exemplifying the 2-transducer arrangement of FIGS. 3 and 4, except that the test wire is too long for end reflections to be of concern, and is moving as opposed to being stationary. The schematic representation is of a system 80 using a transmitter-transducer and a receiver-transducer. Output from a pulser is fed to coil 74 of transducer 82 which generates torsional waves in test wire 30. They move along the longitudinal axis of the wire 30 and reach coil 70 of receiver-transducer 84 which converts them into electrical signals which are impedance matched by transformer 88 and are amplified by amplifiers 90 and 92 and are passed through a bandpass filter (BPF) 94 thereafter. After passing the signals through gated peak detector (GPD) 96 and integrator 98, they are plotted on X—Y plotter 100. Output of bandpass filter 94 is also displayed on an oscilloscope 102. A signal into gated peak detector 96 is used for synchronization with the pulser providing current pulses to transmitter-transducer 82. The test wire, via a coupler 101, is attached to the carriage arm of the X—Y plotter. (Thus the increments in wire position occurring during scanning are equal to the increments in the X-coordinate on the X—Y plot.) FIG. 9 is a diagrammatic representation of a 3-transducer system according to the teachings of the subject invention. As shown in FIG. 9, three transducers 103, 104 and 106 are placed in close proximity of the test wire 30 in a line that is parallel to test wire 30 of length L. Transducer 103 acts as a transmitter whereas transducer 104 is used as a first receiver and transducer 106 is used as a second receiver. All these transducers, as in the preceding setup, are EMT's and are typically bi-directional and acoustically transparent. The distance between 104 and 106 can be made large enough so that the pulses need not overlap in that distance. FIG. 10 shows a simplified schematic representation of a simple version of the velocity scan system wherein a pulse from pulser 110 is used to energize transmitter 103. Pulses 112 and 114 are generated by receivers 104 and 106 respectively and after their respective amplification by amplifiers 116 and 118, respectively, are fed to the inputs $Y_1$ and $Y_2$ of a dual-channel amplifier. By use of suitable time-base units for manual overlapping of the two received pulses, the time-delay data for a torsional wave from wire 30 can be plotted on the Y-axis of XY-recorder 122. A synchronization pulse from pulser 110 such as Velonex 350 is used to trigger oscilloscope 120 such as Tektronix 7704.

Figure 11:
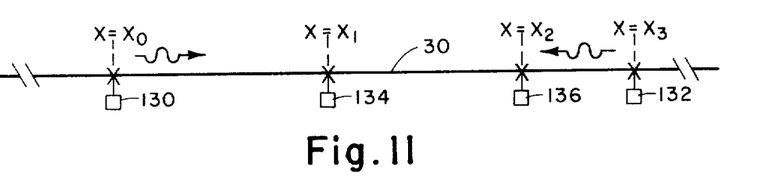
FIG. 11 is a schematic representation of a system using 4-transducer method.
Figure 12:
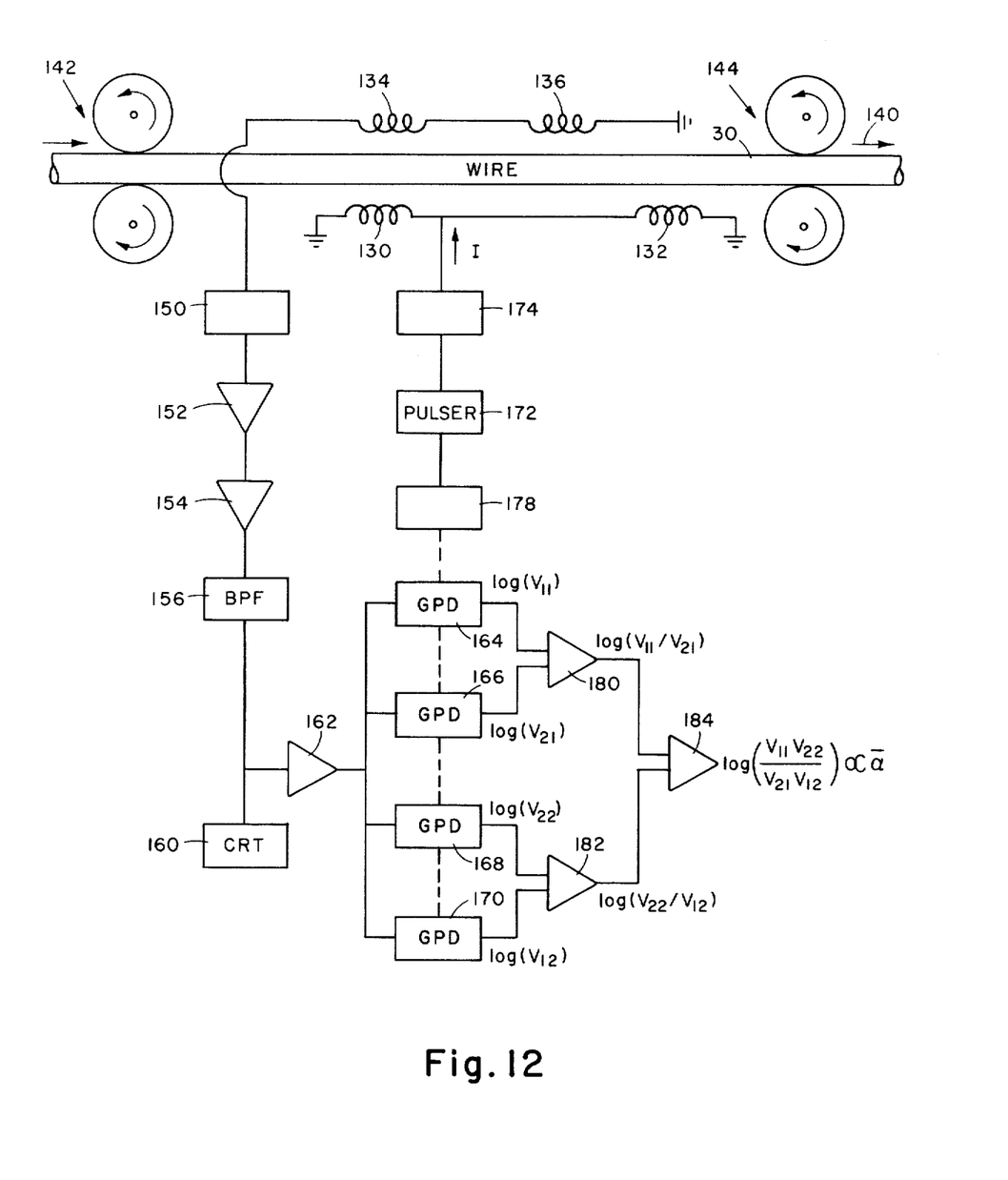
FIG. 12 is a block diagram of 4-transducer method including electronic circuitry.

A 4-transducer setup is shown diagrammatically in FIG. 11. This setup measures accurately attenuation and/or velocity in a test wire 30 of very long length. In this system, transducer 130 acts as a first transmitter and transducer 132 acts as a second transmitter. Transducers 134 and 136 act as the two receivers. The transducers 130, 132, 134 and 136 are placed close to test wire 30 along a line parallel to the axis of the test wire. FIG. 12 shows a block diagram of a system using four transducers. As shown in FIG. 12, test wire 30 is moved in the direction of arrow 140 and is guided by two pairs of rollers 142 and 144. These rollers can be replaced by nylon sleeves or the like. Two transmitter-transducers 130 and 132 sandwich two receiver-transducers 134 and 136; all transducers are placed in line along of the test wire 30. The signals received from transducers 134 and 136 are impedance matched by transformer 150 and are amplified by preamplifier 152 and amplifier 154. The output of amplifier 154 is passed through bandpass filter 156 and then displayed on a CRT 160 and is fed into an AC log circuit 162, the output of which is fed to Gated Peak Detectors (GPD) circuits 164, 166, 168 and 170. Pulser 172 energizes transducers 130 and 132 through an impedance matching transformer 174 and receives a synchronizing signal from synchronizer generator 178 which also provides a synchronizing signal to GPD circuits 164–170. The output of circuits 164 and 166 is combined in difference amplifier 180 and the output of circuits 168 and 170 is combined in circuit 182. Outputs of circuits 180 and 182 are combined in a summing amplifier 184 which has an output which is proportional to the attenuation of the torsional wave $$\overline{\alpha} \propto \ln \frac{(V_{11}V_{22})}{V_{21}V_{12}}$$

in the wire part bounded by receiver-transducers 134 and 136. It should be noted the voltages are of the form $V_{ij}$ where "j" refers to the transmitter involved and "i" to the receiver.

The value of the velocity of the torsional wave is obtained by measuring a difference in two time delay differences as opposed to a single delay difference ($\Delta t$) used in the case of 3-transducer system as described above. Such a difference of the differences would involve four time measurements $t_{ij}$ (at which the peak amplitudes of the pulse voltages $V_{ij}$ occur), just as the attenuation measurement involves four corresponding voltage amplitude measurements. As will be later shown, the velocity $\overline{c}$ for a finite length test wire will be given by $$\overline{c} \propto (t_{12} - t_{22} - t_{11} + t_{21})^{-1}.$$

As for the $\overline{\alpha}$ expression, the expression for $\overline{c}$ is independent of the gap while also applying to the test wire part bounded by receiver-transducers 134 and 136. (It should be noted that the time delays are of the form $t_{ij}$ where "j" refers to the transmitter and "i" refers to the receiver involved.)

We define voltage as the "level" of a given receiver signal after the signal has been appropriately amplified and/or otherwise conditioned. We use the symbol V for voltage. The voltage due to an ultrasound pulse being fired from transmitter "j" and being received by receiver "i" is $V_{ij}$. We assume that the transducer-test wire system is linear, so that, for example, a doubling of input current to a transmitter-transducer results in a doubling of the received voltage. (This is the case for Lorentz forces invoked here as the transduction mechanism.) Then, in the frequency domain (as when data are displayed on the CRT of a spectrum analyser) and roughly in the time domain (as when data are displayed on the CRT of an oscilloscope), this voltage can be regarded as the product of two factors: $V = EF$. Here E gives the contribution from the electronics and from the transducers; F gives the contribution from just the material test medium, as resulting for example from the general tendency of material attenuation to increase with increase in ultrasound frequency. Let E have 3 parts: $E = RST$, where R, S and T refer respectively to the receiver-transducer, electronics (viz., amplifiers), and transmitter-transducer. For clarity, let $F = \exp[-(\overline{\alpha}\Delta X)]$, where $\overline{\alpha}$ is the average attenuation over the test wire distance $\Delta X$ between the transmitter-receiver EMT pair involved.

Refer again to FIG. 11. It can be easily verified that, for transmitter $T_1$ (130) and receivers $R_1$ (134) and $R_2$ (136), $$\frac{V_{11}}{V_{21}} = \frac{E_{11}F_{11}}{E_{21}F_{21}} = \frac{R_1 S_{11} \exp(-\overline{\alpha}_{11}\Delta X_{11})}{R_2 S_{21} \exp(-\overline{\alpha}_{21}\Delta X_{21})}. \tag{a}$$

The result is independent of transmitter factor $T_1$ and thus independent of the transmitter-test wire gap. With $S_{ij} = P_i Q_j$ taken as a product of 2 factors, one for the transmitter electronics ($Q_j$) and one for the receiver electronics ($P_i$), this expression becomes, $$\frac{V_{11}}{V_{21}} = \frac{R_1 P_1 \exp(-\overline{\alpha}_{11}\Delta X_{11})}{R_2 P_2 \exp(-\overline{\alpha}_{21}\Delta X_{21})} \quad \text{(b)}$$

It can also be shown that this reduces to, $$\frac{V_{11}}{V_{21}} = \frac{R_1 P_1 \exp(+\overline{\alpha}\Delta X)}{R_2 P_2} \quad \text{(c)}$$

where $\Delta X$ is the distance between receivers 134 and 136. (The key to deriving this result is in understanding the difference between the average and local values ($\overline{\alpha}$ and $\alpha$ respectively) of attenuation.)

A similar process of reasoning indicates that for transmitter $T_2$ (132) and receivers $R_1$ (134) and $R_2$ (136), $$\frac{V_{22}}{V_{12}} = \frac{R_2 P_2 \exp(+\overline{\alpha}\Delta X)}{R_1 P_1} \quad \text{(d)}$$

Thus, Eqs. (b) and (c) lead to, $$\frac{V_{11}V_{22}}{V_{21}V_{12}} = \exp(+2\overline{\alpha}\Delta X) \quad \text{(e)}$$

and thus to, $$\overline{\alpha} = (2\Delta X)^{-1} \ln \frac{V_{11}V_{22}}{(V_{21}V_{12})} \quad \text{(f)}$$

This result does not depend on $P_i$ or $Q_j$ and so is independent of transducer gaps. Also, by definition, $$\lim_{\Delta X \to 0} \overline{\alpha} = \alpha$$

Thus, one way (but not the only way) to experimentally measure the local value of attenuation involves the choice of small $\Delta X$.

Using an approach similar in spirit to the one used in the preceding calculations, one can also find a gap-independent value of average velocity $\overline{c}$ as, $$\overline{c} = 2\Delta X / [(t_{21} - t_{11}) + (t_{12} - t_{22})].$$

Also, by definition, $$\lim_{\Delta X \to 0} \overline{c} = c.$$

In practice, the agreement between the measurement of c by means of 3-transducer and 4-transducer setups is much closer than the corresponding agreement for $\alpha$ measurements by 3-transducer and 4-transducer setups.

It should be noted that the use of a multiple transducer technique would not be practical without the essentially acoustically transparent nature of the EMT's used. This acoustic transparency is due mostly to the lack of physical contact between the transducers and the test wire and to a lesser extent to the relatively low acoustic efficiency of EMT's. Contacting transducers such as piezoelectric would not be suitable for use in multiple transducer setups. It should further be noted that the gap independence has been tested and confirmed in various experiments with 2-transducer, 3-transducer and 4-transducer setups.

Figure 13:
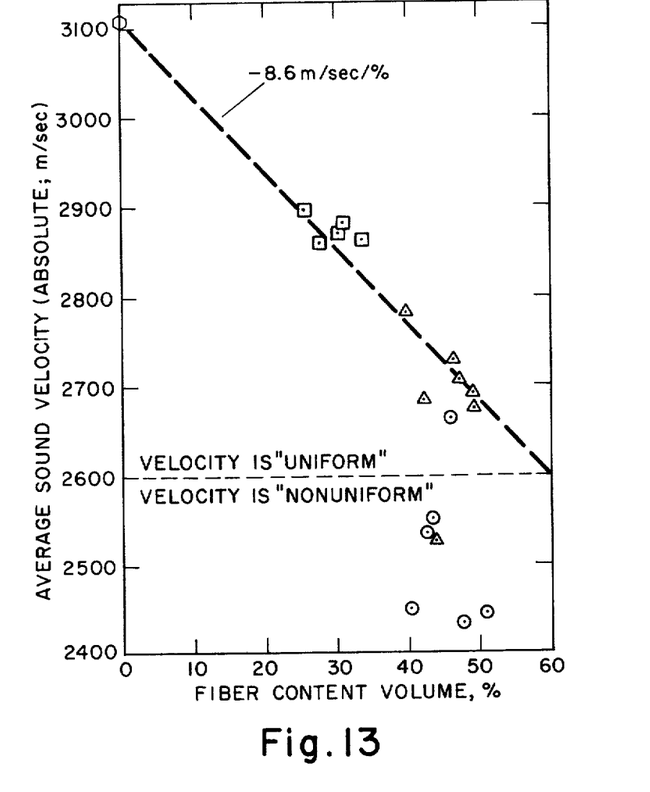
FIG. 13 is a graphical representation of variation of the velocity of torsional waves with a certain characteristic of the test wire.

FIG. 13 indicates the velocity of the torsional wave as a function of percentage of volume of graphite fiber content in a test wire of graphite/aluminum metal matrix composite material using a 3-transducer setup of FIG. 10.

Thus, using the apparatus and the technique described above to measure the velocity and attenuation of a torsional wave generated in moving and/or stationary test wire using EMT's involves measurement of the distance between the transducers and also measuring the amplitude of the electrical pulses received as a result of torsional wave produced in the test wire when electrical pulses of high amplitude currents are passed through the transmitter-transducer coils.

Obviously, many modifications and variations of the present invention are possible in the light of the above teachings. For example, it is possible to use test materials of different configuration (e.g., plates) and of different smoothness and other characteristics. Furthermore, the system and the technique can be used as well for ferromagnetic materials with some modification of the system. Additionally, torsional waves of different mode order and waves of other modes (such as longitudinal) can be produced. Another variation permits the geometrical configuration of the magnet and coil portions of the transducers used as receivers and transmitters can also be varied. Additionally, the wire testing system can also be used for stationary test materials and/or moving test materials. Furthermore, the electronic components forming the wire testing system can be arranged in ways other than the one described above without deviating from the teachings of the subject invention.

It is therefore understood that within the scope of the appended claims the invention may be practiced otherwise than as specifically described.

What is claimed is:

1. An apparatus for nondestructive testing (NDT) an electrically conductive and elongated test material having a longitudinal axis using noncontacting electromagnetic ultrasound transducers (EMT'S) which comprises:

a magnet with pole pieces forming a gap and with the direction of magnetization thereof being generally perpendicular to the longitudinal axis of the test material;

at least one noncontacting electromagnetic ultrasound transducer (EMT) as a transmitter-transducer having the coil thereof adjustably positioned along the longitudinal axis of the test material to have electrical pulses passing therethrough in a direction parallel to the longitudinal axis of the test material and thus generating torsional ultrasound waves in the test material traveling along the longitudinal axis thereof; and at least one more noncontacting electromagnetic ultrasound transducer (EMT) as a receiver-transducer having the coil thereof adjustably positioned colinear with said transmitter-transducer and receiving the torsional ultrasound waves traveling along the longitudinal axis of the test material.

2. The apparatus of claim 1 wherein said transmitter-transducer and receiver-transducer are aligned along the longitudinal axis of said test material.

3. The apparatus of claim 2 which further includes an additional electromagnetic-ultrasound transducer (EMT) to be used as a second transducer-receiver, thus using said apparatus as a 3-transducer setup for studying the properties of said test material.

4. The apparatus of claim 3 which includes one more additional electromagnetic ultrasound transducer (EMT) to be used as a second transducer-transmitter, thus using said apparatus as a 4-transducer setup for studying the properties of said test material.

5. The apparatus of claim 4 wherein said test material is a wire having an uneven outer surface.

6. The apparatus of claim 5 wherein said test material is a composite wire having non-metallic fibers dispersed in a metal matrix.

7. The apparatus of claim 4 wherein each of said first and second transmitter-transducers and said first and second receiver-transducers includes a magnet, a pair of coil forms and a coil wound on said pair of coil forms.

8. The apparatus of claim 4 wherein each of said electromagnetic-ultrasound transducers (EMT's) is bidirectional.

9. The apparatus of claim 4 wherein each of said electromagnetic-ultrasound transducers (EMT'S) is acoustically transparent.

10. A nondestructive testing (NDT) method for studying the properties of a test wire using a plurality of electromagnetic ultrasound transducers (EMT'S) and one or more magnets which includes the steps of:
 arranging the longitudinal axis of said wire generally perpendicular to the direction of magnetic field of said magnet;
 placing a first member of said plurality of EMT'S adjacent to said test wire along the longitudinal axis thereof to act as a transmitter;
 placing a second member of said plurality of EMT'S adjacent to said test wire and colinear with said first member of said plurality of EMT'S to act as a receiver;
 generating a torsional waves in said wire traveling along the axis thereof by electrically exciting said first member of said plurality of EMT'S measuring the velocity and attenuation of said torsional waves by receiving said torsional waves by said second member of said plurality of EMT'S.

11. The method of claim 10 which further includes the step of placing a third member of said plurality of EMT'S colinear with said first and second members of said plurality of EMT'S to act as a second receiver for said torsional waves.

12. The method of claim 11 which further includes the step of placing a fourth member of said plurality of EMT'S to act as a second transmitter for said torsional waves.

* * * * *